(12) United States Patent
Gellerstedt et al.

(10) Patent No.: US 6,642,431 B1
(45) Date of Patent: Nov. 4, 2003

(54) ABSORBENT STRUCTURE HAVING IMPROVED ABSORPTION PROPERTIES

(75) Inventors: Fredrik Gellerstedt, Onsala (SE); Thami Chihani, Mölnlycke (SE); Maria Fernkvist, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/341,826

(22) PCT Filed: Jan. 20, 1998

(86) PCT No.: PCT/SE98/00078

§ 371 (c)(1), (2), (4) Date: Jul. 20, 1999

(87) PCT Pub. No.: WO98/31318

PCT Pub. Date: Jul. 23, 1998

(30) Foreign Application Priority Data

Jan. 21, 1997 (SE) .............................................. 9700158

(51) Int. Cl.⁷ .............................................. A61F 13/15
(52) U.S. Cl. ..................................................... 604/378
(58) Field of Search ................. 604/365, 367, 604/378, 385.28, 391, 381, 375

(56) References Cited

U.S. PATENT DOCUMENTS

| 4,459,396 A | * | 7/1984 | Yamasaki et al. ............ 526/200 |
| 4,885,204 A | * | 12/1989 | Bither et al. ................. 428/913 |
| 5,969,052 A | * | 10/1999 | Mumick et al. ......... 525/329.9 |
| 5,990,377 A | * | 11/1999 | Chen et al. .................... 442/79 |
| 6,107,539 A | * | 8/2000 | Palumbo et al. ............ 604/358 |
| 6,353,149 B1 | * | 3/2002 | Stone .......................... 604/372 |

FOREIGN PATENT DOCUMENTS

| EP | 0 158 914 | | 10/1985 |
| EP | 0 536 941 A1 | * | 9/1992 |
| EP | 0 536 941 | | 4/1993 |
| WO | WO 93/15702 | * | 8/1993 |

\* cited by examiner

*Primary Examiner*—Weilun Lo
(74) *Attorney, Agent, or Firm*—Young & Thompson

(57) ABSTRACT

An absorbent, porous structure (4), intended for use in an absorbent article, wherein the structure (4) exhibits a first region (19), primarily consisting of a first material, which stands in direct connection with a second region (20), primarily conssisting of a second material. The receding wetting angle $\theta_r$ is larger for the first material than for the second material, whereby liquid transport between the two regions (19, 20) takes place in a direction from the first region (19) to the second region (20), at least when the porous structure (4) is wet.

24 Claims, 4 Drawing Sheets

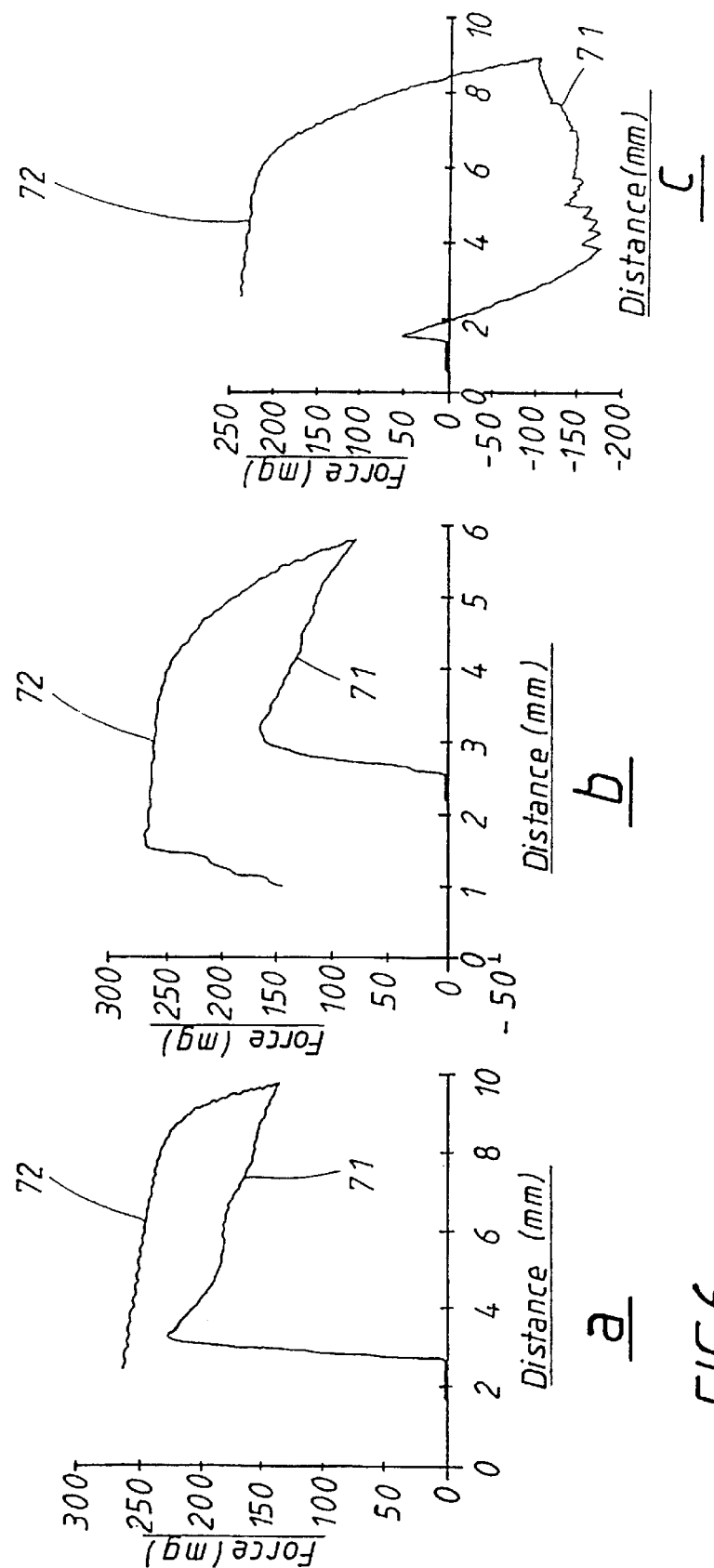

ABSORBENT STRUCTURE HAVING IMPROVED ABSORPTION PROPERTIES

TECHNICAL FIELD

The invention pertains to an absorbent, porous structure, intended for use in an absorbent article, wherein the structure exhibits a first region, primarily consisting of a first material, which stands in direct connection with a second region, primarily consisting of a second material.

BACKGROUND OF THE INVENTION

A large problem, in connection with the construction of absorbent bodies for absorbent articles of the discussed type, is to achieve an optimum combination of a sufficiently large liquid acquisition ability, sufficient local and total absorption capacity and sufficient liquid distribution ability. Furthermore, it is essential that the absorbent article is able to retain absorbed body fluid so that rewetting, i.e. liquid passage back out from the article, is avoided. Another important property of, above all, diapers and incontinence protectors is that the article repeatedly should be able to receive and absorb relatively large liquid quantities, emitted during a short period of time.

One type of commonly occurring absorbent bodies for absorbent articles consists of one or several layers of cellulose fluff pulp. When such an absorbent body is wetted, the region of the absorbent body which initially is hit by the liquid will absorb essentially all liquid. Thereby, this region is saturated with liquid and, when subsequent wettings occur, the absorbent body does not have sufficient capacity in order to receive all excreted body fluid. Accordingly, the liquid will flow out over the surface of the article and leak out over the edges of the article.

In order to remedy such leakage, it has been suggested to provide the absorbent body with compression patterns of different types and thereby to increase the liquid distribution ability of the article. One example of such a compression pattern is grooves which extend in the longitudinal direction of the article. In this way, it is possible to achieve a certain drainage of the initially wetted region on the absorbent body, since the finer capillaries in the compressed portions of the absorbent body transport liquid better than the surrounding portions of the absorbent body. Such capillary transport, however, takes place slowly and the draining of the wetted region of liquid will therefore often be incomplete and insufficient.

Another problem, in connection with compressed fibre structures, is that the compressed regions swell when wetted, whereas surrounding, less compressed regions often collapse. Thereby, the initial differences in capillary size in the structure are levelled out, and the liquid distribution ability of the fibre structure is impaired.

One way of avoiding that liquid flows out onto the surface of the absorbent body is to arrange two or more absorbent layers with mutually different properties on top of each other. For example in accordance with WO 93/15702, an upper layer, intended to be facing the user during use, may thereby consist of cellulose fluff pulp with a high critical bulk and a comparatively coarse capillary network, while a lower layer consists of a layer of cellulose fluff pulp with lower critical bulk and finer capillaries. Thereby, critical bulk refers to the bulk at which the fluff pulp neither swells nor collapses when wetted.

The intention with such a construction is that the liquid rapidly should be allowed into the upper, more porous layer, and then gradually be emptied of liquid by means of the upper layer being drained by the finer capillaries in the lower layer. The expectation is that the upper layer should be sufficiently emptied of liquid in order to avoid leakage when the absorbent body once again is hit by body fluid. However, it has been found that in practice this will not work as expected. The reason for this is that the surface properties of the fibres in the two cellulose fluff layers are such that liquid drainage from the upper layer to the lower layer does not take place to the extent which might be expected from the difference in capillary size.

One type of cellulose fluff pulp with high critical bulk is chemi-thermomechanically manufactured fluff pulp, so-called CTMP. In a structure of the type which is disclosed in WO 93/15702, CTMP is combined with chemically manufactured fluff pulp, so-called CP, which has a lower critical bulk. Such pulps initially also exhibit a difference in hydrophilicity, or wettability, wherein CTMP is less hydrophillic than CP. Such a difference in hydrophilicity facilitates the liquid transport in a direction from a region consisting of CTMP to a region consisting of CP.

During wetting, however, the surface properties of the cellulose fibres change, so that also cellulose fluff pulp which in a dry state exhibits low wettability instead becomes more hydrophillic. The reason for this, amongst other things, is that the surface-chemical properties of the pulp fibres are changed because a reorientation occurs at the fibre surfaces so that hydrophillic groups are concentrated, as a result of which the fibre surfaces become more wettable. Another reason, contributing to the changed surface properties, is that a change takes place also with regard to resins and other components, for example by means of certain components dissolving, while other, more hydrophillic components migrate towards the fibre surfaces.

SUMMARY OF THE INVENTION

By means of the present invention, however, an absorbent structure of the type mentioned in the introduction has been achieved in which the problems with liquid transfer between the regions in the absorbent body, consisting of absorption materials with different surface properties, have been essentially eliminated.

An absorbent structure according to the invention is primarily characterized in that the receding wetting angle $\theta_r$, is larger for the first material than for the second material, as a result of which liquid transport between the two regions takes place in a direction from the first region to the second region when the porous structure is wet.

According to one advantageous embodiment, also the advancing wetting angle $\theta_a$ is larger for the first material than for the second material, as a result of which liquid transport takes place from the first region to the second region, irrespectively of whether the structure is dry or wet.

It is advantageous for the liquid transfer between the regions in the absorbent structure if the average pore size in the absorbent structure is larger within the first region with the first material than within the second region with the second material. Since, for example, a porous fibre material exhibits pores, or voids with different sizes within a size interval, it is impossible to define an exact pore size. The expression "average pore size" refers to an average of the size of the pores in the absorbent structure. Thereby, it is desirable that the majority of the pores have a size which is close to the average pore size. This implies that the pore size variation is small and that the liquid transportation properties of the structure are easier to predict, based on the knowledge of the average pore size.

According to one embodiment of the invention, the first region is constituted of a first layer in the absorbent structure, and the second region is constituted of a second layer in the absorbent structure, wherein the two layers stand in direct connection with each other via surfaces of the layers bearing on each other.

Alternatively, the two regions can be constituted of parts of the one and the same material layer. Thereby, the division of the material layer into different regions may be such that the first region and the second region are arranged next to each other in the plane of the material layer. However, it is also possible to design an absorbent structure according to the invention exhibiting a material layer where the two regions of material with different surface properties are arranged next to each other in the thickness direction of the material layer.

Still another possibility, within the scope of the, invention is to arrange a number of regions with mutually different receding wetting angles, so that a wetting angle gradient is formed in the absorbent structure. Such a wetting angle gradient may occur in a substantially planar absorbent structure, exhibiting a thickness direction and two opposing main surfaces. Thereby, a wetting angle gradient in the thickness direction of the structure may be achieved by means of the structure being built up from a number of layers, wherein the receding wetting angle decreases in a direction from one surface of the structure towards the other surface.

In a corresponding way, a wetting angle gradient may be created in the plane of the structure by means of arranging regions with different receding wetting angles next to each other in the plane. It is of course also possible within the scope of the invention to conceive a structure exhibiting a wetting angle gradient both in the thickness direction and in the plane.

It is further an advantage if the regions in the structure also exhibit a gradient in the advancing wetting angle.

According to another embodiment of the invention, the first material in itself exhibits a receding wetting angle which is essentially as large as, or smaller than the receding wetting angle of the second material. In order to achieve the desired difference in wetting angles between the two material regions in the absorbent structure the first material is treated with an agent in order to raise the receding wetting angle above the value of the receding wetting angle of the second material.

The invention has been found to be well suited in connection with absorbent structures wherein the first region primarily consists of chemi-thermomechanical cellulose fluff pulp (CTMP), and the second region consists of chemical cellulose fluff pulp (CP), and wherein the surface of the CTMP fibres has been treated with an agent in order to increase the receding wetting angle. With such a treatment of CTMP fibres it has been found to be possible to raise the receding wetting angle from between 0°–10° to approximately 40°, something which gives the absorbent structure considerably improved liquid transportation properties by means of favourably influencing the liquid transfer between adjacent regions with different fibre structure.

Other absorption materials which may be used when designing an absorbent structure according to the invention are different types of absorbent foams, absorbent, bonded or unbonded fibre structures completely or partly consisting of absorbent fibres such as cotton, viscose, peat moss, flax, or the like.

A useful agent for raising the receding wetting angle is ethyl-hydroxy-ethylcellulose (EHEC) which is applied in the absorbent structure, for example by spraying or coating with a liquid containing the agent, for example in the form of a solution or suspension, or by any other known method for surface treatment.

The absorbent structure according to the invention may further constitute all or a part of an absorbent body in an absorbent article, such as a diaper, a sanitary napkin, or an incontinence protector. Such an absorbent article exhibits a liquid-pervious cover layer, a liquid-impervious cover layer, an absorbent body enclosed between the two cover layers. In a case where the first region is constituted of a first layer in the absorbent body and the second region is constituted of a second layer in the absorbent body, the first layer is suitably facing the liquid-pervious cover layer and the second layer is facing the liquid-impervious cover layer.

As a rule, an absorbent article has an elongate shape with two end portions and a crotch portion, arranged between the end portions, intended to be arranged in the crotch of a user during the use of the article and thereby to serve as a reception region for the body fluid which is emitted to the article. Thereby, it is advantageous that the first region, consisting of the first material, substantially coincides with the crotch portion of the article.

By means of ensuring that the material regions in the absorbent structure exhibit differences in wetting angles at least in a wet state, but preferably also in a dry state, it is possible to obtain a controlled and predictable liquid distribution in the absorbent structure.

When a liquid droplet is placed on an even surface in a solid state, one out of two possible events will take place depending on the properties of the liquid and the solid material, respectively. The liquid may either be spread out over the surface, or remain as a droplet on the solid material. In the latter case, the droplet will form a defined angle with the surface of the solid material.

Theoretically, the contact angle $\theta$ may adopt values between 0° and 180°. In practice, however, the contact angle will never become 180° since the force of gravity disturbs the shape of the droplet. A contact angle $\theta=0°$ will imply that the liquid spreads spontaneously on the surface. The contact angle $\theta=90°$ constitutes the limit for wetting. When the contact angle is smaller than 90°, liquid will spontaneously be absorbed into the pores of the material, while a contact angle above 90° implies that a pressure must be applied in order to make the liquid penetrate into the pores. However, the limit of 90° is true only for capillaries having parallel walls.

Dynamic contact angle refers to the angle which is exhibited when a liquid front is moving. The terms advancing and receding wetting angle are intended to specify if the dynamic contact angle is measured when a liquid advances across a dry surface, or when the liquid recedes across a recently wetted area.

The significance of the receding wetting angle, to the achievement of good liquid transfer between two components in an absorbent structure, has not previously been known. By providing a sufficiently large difference between the receding wetting angles of adjacent regions in an absorbent structure it is, accordingly, by means of the invention possible to construct an absorbent fibre structure wherein the liquid transfer properties do not change when the fibre structure is wetted. As a result of the difference in receding wetting angle, between the different regions in the fibre structure, the region which has the smallest wetting angle further has the ability to drain liquid from a region in the fibre structure with a higher receding wetting angle.

The liquid transfer between two adjacent regions in a fibre structure also depends on the pore size in the two regions. If the regions have the same pore size, the difference in receding wetting angle must be larger the smaller the pores are. This also implies that a very strongly compressed structure with small pores, in certain cases may drain a more hydrophillic, less compressed structure. In practice, however, it has been found that differences in pore size are levelled out after wetting. The reason for this is that wet structures swell or collapse so that two fibre structures which initially have different pores sizes become rather similar after wetting.

BRIEF DESCRIPTION OF THE DRAWINGS

In the following, the invention will be described more closely with reference to the figures which are shown in the attached drawings, in which

FIG. 5 is a schematic illustration of an instrument arrangement for the determination of contact angle and FIGS. 6a–6c show examples of the graphs which are recorded during the determination of contact angle.

DETAILED DESCRIPTION OF PREFERRED EMBODIMENTS

Figure 1:
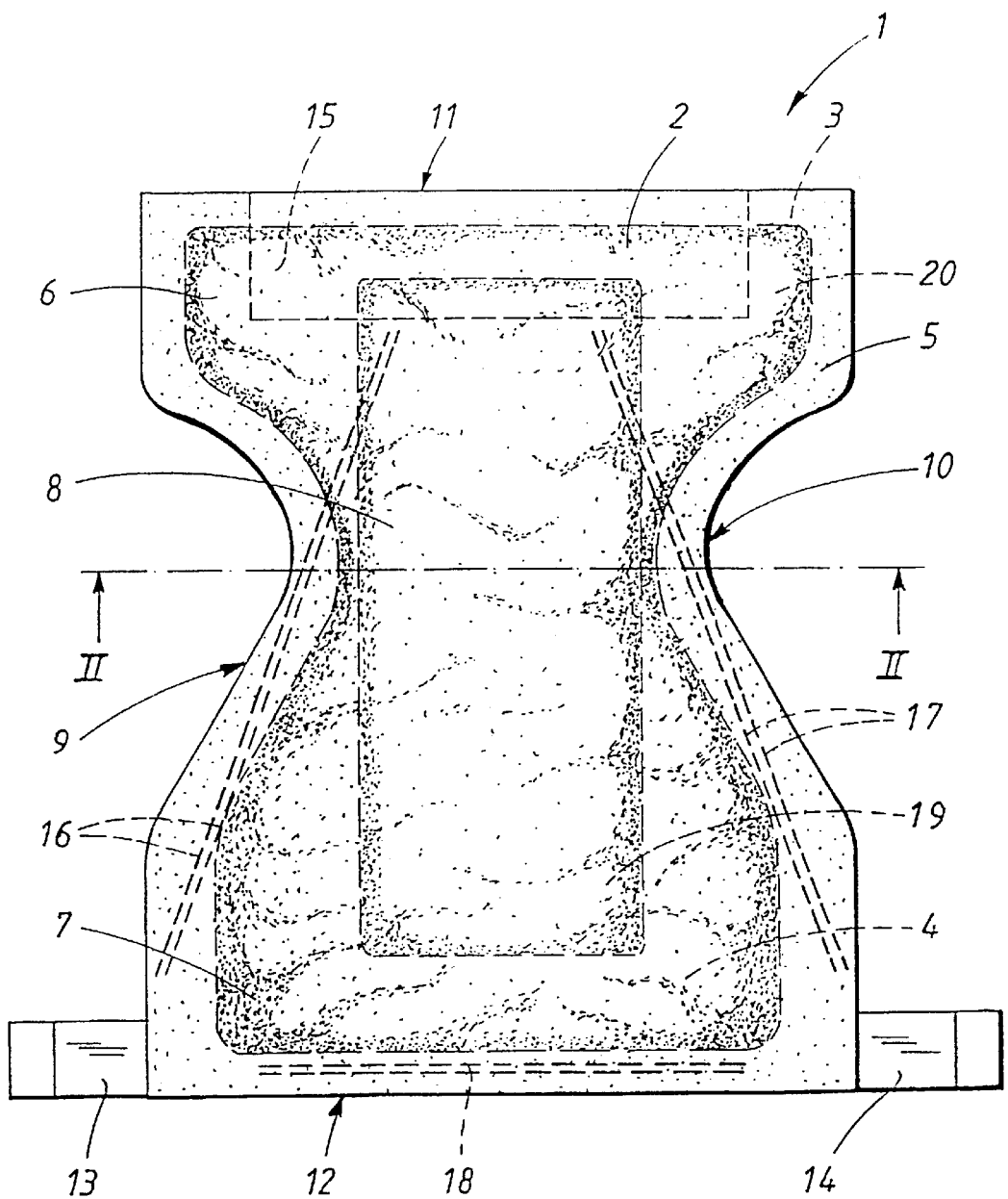
FIG. 1 shows a plan view of a diaper seen from the side which is intended to be facing the user during use.
Figure 2:
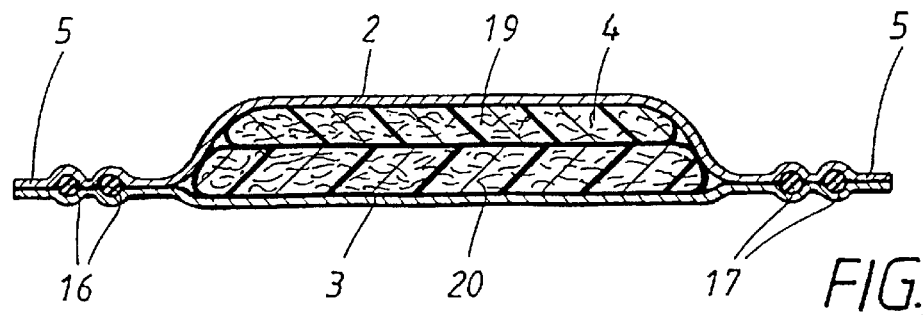
FIG. 2 shows a section through the diaper in FIG. 1, taken along the line II—II.

The diaper 1 shown in FIGS. 1 and 2 comprises a first liquid-pervious cover layer 2, a second liquid-impervious cover layer 3, and an absorbent body 4 enclosed between the cover layers. The two cover layers 2, 3 have a slightly larger extension in the plane than the absorbent body 4 and project out past the absorbent body 4 around its entire periphery. The cover layers 2, 3 are mutually connected within the projecting portions 5, for example by gluing or welding with heat or ultrasonics.

The liquid-pervious cover layer 2 is for example constituted of a layer of non-woven fibre fabric, so-called nonwoven material, or of a perforated plastic film, a scrim material, or the like. The cover layer 2 may of course also consist of a laminate of two or several layers of any one or any of the listed materials.

The liquid-impervious cover layer 3 may consist of a liquid-impervious plastic film, a nonwoven layer which has been coated with a liquid barrier material, or any other easily pliable material layer having the ability to resist liquid penetration. As a rule, it is an advantage if the liquid-impervious cover layer 3 exhibits a certain breathability, i.e. allows passage of water vapour through the layer 3.

The diaper 1 has an elongate shape, with wider front and rear portions 6, 7 and a narrower crotch portion 8. The front portion 6 is the part of the diaper 1 which is intended to be facing forwards on the user when the diaper is used and the rear-portion 7 is the part of the diaper which faces backwards on the user. Furthermore, the diaper 1 has two longitudinal, concavely-curved side edges 9, 10, a front edge 11 and a rear edge 12.

The diaper 1 is of the type which is attached together during use, so that it in a pant-like way encompasses the lower portion of the torso of the user. For this purpose, a tape flap 13, 14 is arranged projecting from each side edge 9, 10, close to the rear edge 12 of the diaper. The tape flaps 13, 14 are intended to interact with a reception area 15, arranged on the liquid-impervious cover layer 3, on the front portion 6 of the diaper 1. Such a reception area 15 suitably exhibits some kind of reinforcement, for example in the form of an additional plastic layer, or a coating applied on the liquid-impervious cover layer 3. Alternatively, it is of course possible to conceive the use of other types of attachment devices for the diaper 1, such as buttons and buttonholes, hooks and eyes, snap fasteners, hook and loop closing devices, or the like.

The diaper 31 is further provided with pre-tensionally applied, longitudinal elastic members 16, 17, arranged in a substantially V-shaped pattern, with the tip of the V directed towards the front edge 11 of the diaper and the two legs directed towards the rear edge 12 of the diaper. The elastic members 16, 17 shape the diaper 1 and constitute its leg elastics during the use of the diaper. Thereby, the elastic members 16, 17 serve to keep the side edges 9, 10 of the diaper bearing on the legs of the user, in order to prevent gaps from arising between the diaper and the body of the user during use, through which gaps body fluid can leak out of the diaper.

In a corresponding way, an elastic member 18 is arranged along the rear edge 12 of the diaper in order to achieve an elastic sealing around the waist of the user. The absorbent body 4 consists of two absorption layers 19, 20 with mutually different composition. The first absorption layer 19 is arranged immediately inside the liquid-pervious cover layer 2, and the second absorption layer 20 is arranged nearest to the liquid-impervious cover layer 3. The absorption layers have mutually different shape and size, wherein the first absorption layer 19 is smaller than the second absorption layer 20 and has a substantially rectangular shape, whereas the second absorption layer is T-shaped, with the crossbeam of the T at the front portion 6 of the diaper.

The first absorption layer 19 primarily consists of cellulose fluff pulp manufactured in a chemi-thermomechanical way, henceforth called CTMP. A layer of such fluff pulp has a relatively open structure, with relatively large capillaries, since CTMP fibres are stiff and rather course. The structure remains to a great extent also after wetting, since the fibres maintain a large portion of their stiffness. Accordingly, an absorption layer 19 of CTMP fibres has a high instantaneous liquid acquisition ability, good liquid retention ability, but comparatively low liquid wicking ability.

The second absorption layer 20 primarily consists of cellulose fluff pulp which has been manufactured in a chemical way, henceforth called CP. The fibres in such a fluff pulp are thin and pliable and form a fibre structure with relatively small capillaries when formed into a layer. An absorption layer of CP fibres has high liquid wicking ability but absorption into the layer 20 proceeds slowly because of the small capillaries. Furthermore, the liquid volume which can be absorbed into a structure of CP fibres is limited, especially since the fibres collapse when they are wetted.

By means of their mutually different properties the two absorption layers 19, 20 fulfil different functions. Thereby, the first absorption layer serves as a reception layer for the liquid which is emitted to the diaper 1. The first absorption layer 19 should be able to rapidly receive large liquid quantities during a short period of time, i.e. have a high instantaneous liquid absorption ability. The layer 19 should further be able to retain the liquid until it is successively absorbed by the second absorption layer 20. Thereby, the second absorption layer 20 constitutes a storage and distribution layer for the liquid. The liquid which is absorbed by the second absorption layer 20 is distributed through the capillary structure of the layer, away from the region of the layer which initially is wetted by the liquid. As a result of this, new liquid can gradually be absorbed from the first absorption layer, i.e. from the first absorption layer 19 to the second absorption layer 20.

In order to make it possible to utilize the construction with two absorption layers 19, 20, having different absorption properties in the intended way, it is essential that the liquid always is transferred from the first absorption layer to the second absorption layer. This implies that the liquid affinity of the second absorption layer 20 has to be higher than the liquid affinity of the first absorption layer 19, in order to ensure that liquid transfer between the layers 19, 20 always takes place in the correct direction.

Untreated CTMP fibres usually exhibit an advancing wetting angle, $\theta_a$, which during wetting with water is between 40° and 60°, whereas the receding wetting angle, $\theta_r$, is between 0° and 20°. Corresponding values for CP fibres (chemical pulp) are $\theta_a$ between 20° and 30° and $\theta_r$ approximately 0°. This implies that as long as the fibre structure is dry, liquid transport occurs in a direction towards the second absorption layer 20, since the advancing wetting angle is larger in the second absorption layer 20 than in the first absorption layer 19. As soon as the layers are wet, however, there is no difference in wetting angle and the liquid transport between the layers therefore comes to a stop. Accordingly, the expected drainage of liquid from the first absorption layer 19 to the second absorption layer 20 does not occur.

In order to ensure that liquid transport takes place in a direction from the first absorption layer 19 to the second absorption layer 20, the CTMP fibres of the first absorption layer 19 have, in accordance with the invention, been treated in order to increase the receding wetting angle $\theta_r$. Such an increase of $\theta_r$ may, for example, be achieved by treating the cellulose fibres with an agent which increases $\theta_r$.

Some examples of agents which may be used in order to increase Or are polymers such as ethyl-hydroxy-ethyl cellulose, henceforth abbreviated to EHEC, polyvinyl alcohol (PVA) and poly-n-isopropylacryloamide (PNIPAM). Other useful agents are different polysaccharides, cellulose derivatives, surfactants anchored on the surface of the absorption material and polymeric surfactants.

As earlier discussed, the wetting angle-increasing agent can be applied on the fibres by means of any known technique for surface treatment of fibres. Accordingly, the agent may for example be sprayed or in another way be applied on the fibres in the form of a liquid containing the agent.

The increase of the receding wetting angle $\theta_r$, which is obtained when treating CTMP with EHEC, is of the magnitude of 40°. Since the CP fibres have a receding wetting angle $\theta_r$ which is 0°, the liquid transport in the absorbent body 4 will always take place in a direction from the first absorption layer 19 to the second absorption layer 20.

Figure 3:
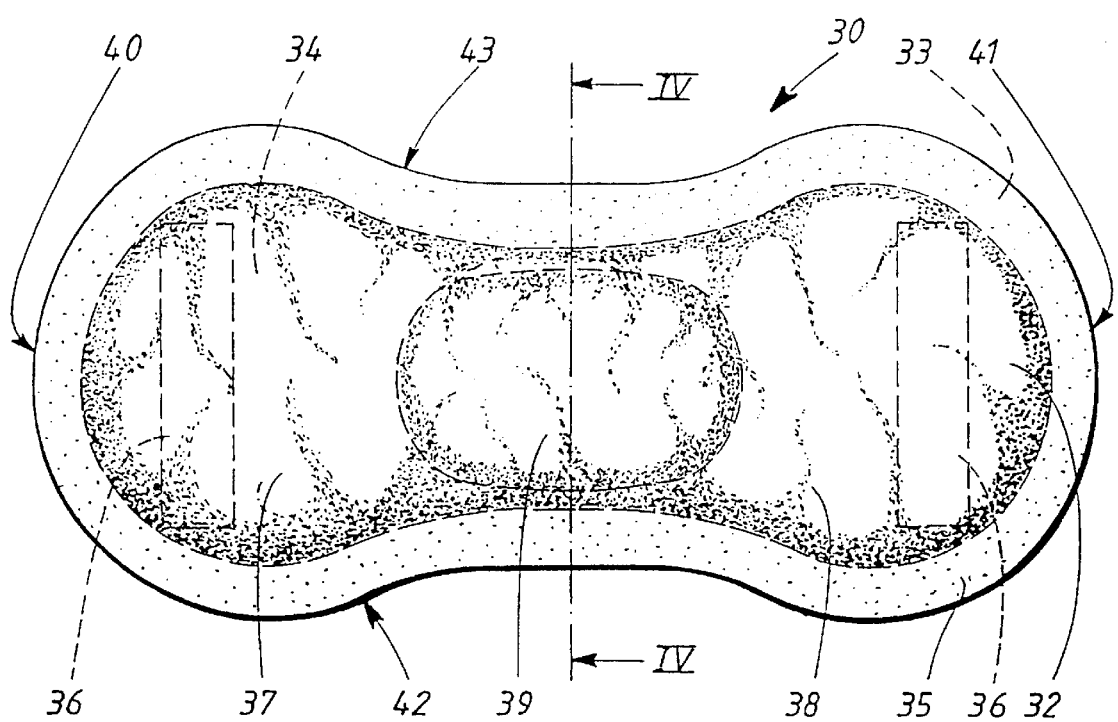
FIG. 3 shows a plan view of an incontinence protector, seen from the side which is intended to be facing the user during use.
Figure 4A:
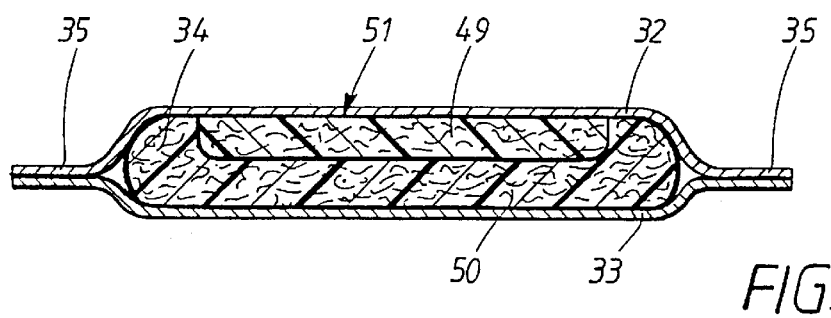
FIG. 4a shows a section along the line IV—IV through the incontinence protector in FIG. 3, and presenting an absorbent body according to a first embodiment of the invention.
Figure 4B:
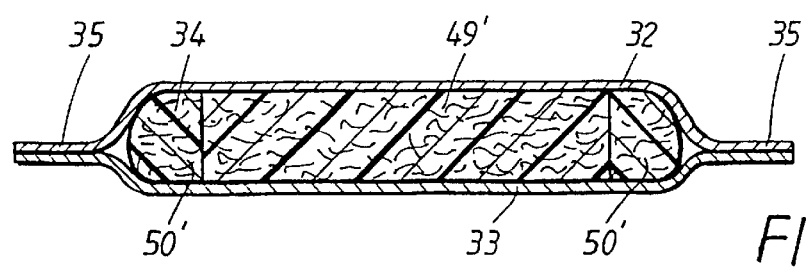
FIG. 4b shows a section along the line IV—IV through the incontinence protector in FIG. 3, and presenting an absorbent body according to a second embodiment of the invention.

The incontinence protector 30, shown in FIGS. 3, 4a and 4b, comprises a liquid-pervious cover layer 32, a liquid-impervious cover layer 33, and an absorbent body 34 enclosed between the cover layers 32, 33. The liquid-pervious cover layer 32 is, for example, constituted of a layer of non-woven fibre fabric, so called nonwoven material, or of a perforated plastic film, a scrim material, or the like. The liquid-impervious cover layer 33 may consist of a liquid-impervious plastic film, a nonwoven layer which has been coated with a liquid barrier material, or any other easily pliable material layer which has the ability to resist liquid penetration. Generally, it is an advantage if the liquid-impervious cover layer 33 exhibits a certain breathability, i.e. allows passage of water vapour through the layer 33. The two cover layers 32, 33 have a somewhat larger extension in the plane than the absorbent body 34 and extend a distance out past the absorbent body 34 around its entire periphery. The cover layers 32, 33 are mutually connected within the projecting portions 35, for example by gluing or welding with heat or ultrasonics.

On the outside of the liquid-impervious cover layer 33, an attachment member 36 in the form of two transverse regions of self-adhesive glue is arranged. Before use, the attachment member 36 is suitably covered with a detachable protective layer, not shown in the drawing, out of paper treated with release agent, plastic film, or the like. Instead of the shown glue pattern, in the form of two transverse glue regions, a number of other glue patterns may be used, such as one or several longitudinal regions, dots, complete coverage etc. Alternatively, other types of attachment members may be utilized, such as hook and loop surfaces, snap fasteners, girdles, special underpants, or the like.

An incontinence protector 30 of the type shown in the figures is primarily intended to be used by persons with relatively light incontinence troubles and therefore has such a size that it easily can be accommodated inside a pair of regular underpants. Thereby, the attachment member 36 serves to keep the incontinence protector in place inside the underpants.

The incontinence protector 30 is substantially hourglass-shaped, with wider end portions 37, 38 and a narrower crotch portion 39, located between the end portions 37, 38. The crotch portion 39 is the portion of the incontinence protector 30 which is intended to be applied in the crotch of the user during use and serve as a reception area for the body fluid which is excreted to the incontinence protector 30. Furthermore, the incontinence protector 30 exhibits two transverse, rounded end edges 40, 41, and two longitudinal curved side edges 42, 43, extending between the end edges 40, 41.

In FIGS. 4a and 4b two alternative constructions of the absorbent body 34 of the incontinence protector 30 in FIG. 3 are shown.

The absorbent body 34 shown in FIG. 4a is constituted of a coherent absorption layer exhibiting a first region 49, primarily consisting of a first type of fibres, and a second region 50, primarily consisting of a second type of fibres. The first region 49 has an essentially oval shape and is in the plane of the absorbent body 34 substantially located at the crotch portion 39 of the incontinence protector 30. In the thickness direction of the absorbent body, the first region 49 extends from the liquid-pervious cover layer 32 of the incontinence protector 30, a distance in direction towards the liquid-impervious cover layer 33, but not all the way to the liquid-impervious cover layer 33. Thereby, the first region 49 is encompassed by the second region 50 everywhere, except at the surface 51 of the first region 49 which is facing towards the liquid-pervious cover layer 32.

The first region 49 of the absorbent body primarily consists of a fibre material which, in comparison to the second region 50, has a higher wetting angle both in a wet and in a dry state. This implies that both the advancing wetting angle $\theta_a$ and the receding wetting angle $\theta_r$ are higher for the first region 49 than for the second region 50. Such a difference in wetting angle can either be achieved by choosing materials which from the outset exhibit a sufficient difference in the magnitude of the wetting angles. Alternatively, the difference can be achieved by treating the material in either one or both regions 49, 50 with an agent in order to change the wetting angles. Suitable agents for this purpose have been described in connection with the diaper shown in FIGS. 1 and 2.

It is not necessary that the material in the regions 49, 50 is constituted of different types of materials, but the absorbent body can be constituted by a single material layer where the difference in at least the receding wetting angle of the different regions has been achieved by means of treating the material in one or in both regions 49, 50 so that the surface properties of the absorption material have been changed.

Also the absorbent body 34', shown in FIG. 4b, exhibits a first region 49' and a second region 50'. The only difference between the absorbent bodies 34, 34' in FIGS. 4a and 4b is that the first region 49' in the latter FIG. 4b extends through the entire thickness of the absorbent body 34'.

Determination of Wetting Angles

Figure 5:
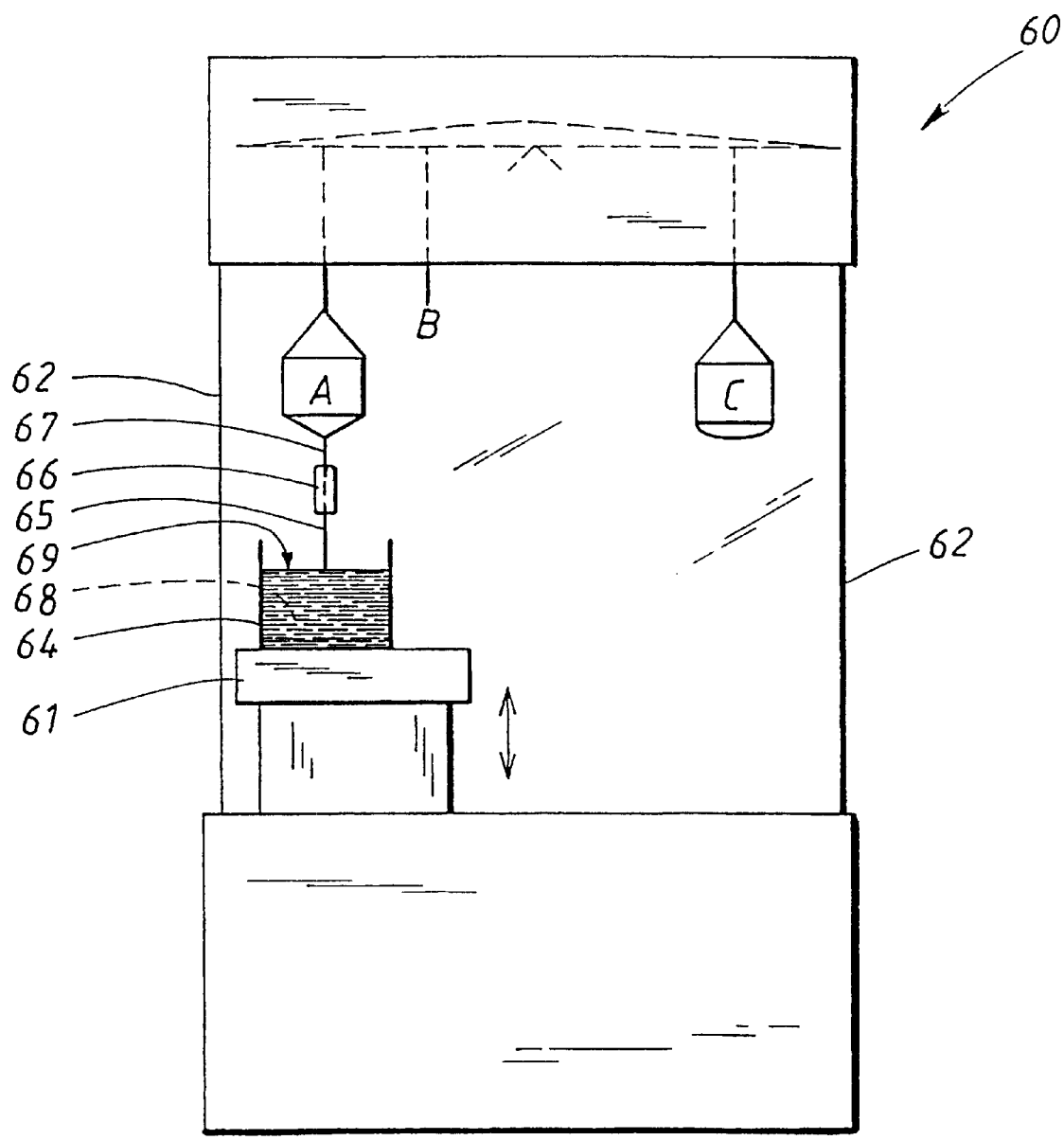

The different wetting angles which are important to the invention were determined by means of the apparatus shown in FIG. 5. Thereby, Wilhelmy's method was used.

The balance which was used for the determination of contact angles in connection with the invention, is manufactured by Cahn instruments in California, U.S.A. The model number is DCA-322, where DCA stands for "Dynamic Contact Angle". A PC, Compaq 386/20, was used for controlling the instrument. The same computer was also utilized for recording data from the measurements and for performing the subsequent calculations.

During a measurement, a fibre 65 is vertically suspended in an extremely sensitive balance 60. A liquid container 64 is placed on a mobile table 61, directly below the fibre 65. By means of the table 61 being elevated, the liquid surface 69 moves upwards towards the fibre 65. When the fibre 65 is dipped into the liquid 68, a liquid meniscus, which affects the partially immersed fibre with a vertical force, is formed around the fibre 65.

The force which arises between the liquid 68 and the fibre 65 may either be positive or negative, depending on the surface properties of the liquid and the fibre. An attracting force, i.e. a positive force, arises when the contact angle between fibre and liquid is smaller than 90°. When the system exhibits a contact angle larger than 90°, on the other hand, liquid and fibre will repel each other and the force becomes negative. The latter is valid, for example, for a polypropylene fibre which is immersed into distilled water.

The attracting or repulsing force is measured by means of the balance. The force is related to the contact angle according to:

$$F = \gamma_L p \cos\theta + m g - \rho_L l g A;\text{ wherein}$$

F = the measured force [N]
$\gamma_L$ = the surface energy of the liquid [J/M$^2$]
p = the circumference of the fibre [m]
$\theta$ = the contact angle in the interface fibre-liquid-air [°]
m = the mass of the mounted fibre [kg]
g = the constant of gravitation [m/s$^2$]
$\rho_L$ = the density of the liquid [kg/m$^3$]
l = the wetted fibre length [m]
A = the cross-sectional area of the fibre [m$^2$]

The contact angle may vary along and around the fibre, and an average calculated on the entire periphery of the fibre is intended in the equation.

The second term in the equation represents the weight of the mounted fibre, while the third term of the equation is the so-called "buoyancy-force", i.e. the weight loss which arises as a result of displaced liquid volume. In a computer (not shown) furnished with a calculation program for contact angle determination, usually both these two terms are taken into account, something which simplifies the equation to:

$$F = \gamma_L p \cos\theta$$

When the fibre 65 is immersed into the liquid 68 the value of the advancing contact angle $\theta_a$ is obtained. In order to obtain a value of the receding contact angle $\theta_r$, the fibre 65 is lifted up from the liquid 68 by means of lowering the mobile table 61.

The contact angles $\theta_a$, $\theta_r$ are dependent on the velocity of the liquid front, and it is therefore important that the mobile table 61 is elevated and lowered with a constant speed. Furthermore, the speed must be sufficiently low in order to enable the system to have time to reach equilibrium in each point during the measurement.

Furthermore, the temperature and the moisture in the sample chamber should be controlled.

The balance 60 has three pans of a balance (see FIG. 5). A first pan A has an accuracy of 10$^{-6}$ g, which makes it suitable for contact angle measurement on fibres. However, the balance may also be used for surface energy measurements on liquids, at which a less accurate second pan B is used. The balance is tared by means of placing counterweights in a third pan C.

In order to prevent draughts, dust, or the like, from disturbing the measurement, the pans and the mobile table 61 are protected by sliding glass frames 62. These also enable control of air moisture and temperature. In order to avoid disturbing vibrations during the course of the measurement, the balance is placed on a foundation (not shown).

The table which the liquid container 64 stands on is elevated and lowered by means of a motor (not shown). The speed of the table 61 is controlled by the connected computer and is displayed before a measurement is started, Other parameters which have to be fed in before the measurement is started are the surface energy of the liquid and the circumference of the fibre 65.

A fibre is mounted on a tape piece 66 so that a portion of the fibre 65 is free. The mounted fibre 65 is attached in a metal clamp 67 and is suspended in the first pan A. The balance 60 has first been tared with only the metal clamp 67 being suspended in the pan A. Test liquid 68, having a known surface energy, is placed in the liquid container 64 on the table 61 below the fibre 65. The fibre 65 should be suspended perpendicularly to the liquid surface 69 and has to be completely still before the measurement starts so that the balance shows a stable value. The table 61 with the liquid container 64 is elevated so that the liquid surface 69 is approximately 1 mm from the fibre 65.

When the measurement is started, the computer records a base line, whereafter the table 61 is elevated with a predetermined speed. Thereby, the fibre 65 has to be sufficiently stiff in order to remain vertical also after it has penetrated the liquid surface 69. When (depending on the length of the fibre) a millimetre or so or a few millimetres of the fibre 65 has been dipped down into the liquid 68, the computer is commanded to stop the table 61. Thereafter, the table 61 is lowered. During the course of the test, the variations of the force along the fibre 65 are shown on the display of the computer. Examples of how the obtained graphs may look are shown in FIGS. 6a–c. When the measurement is completed, representative portions of the advancing 71 and the receding graph 72 are selected. Thereafter, the computer calculates contact angles with the aid of Wilhelmy's equation.

The invention should not be regarded as being limited by the herein described embodiments. Accordingly, the invention includes all types of absorbent structures comprising at least two communicating regions of which at least the receding wetting angle is different.

Further, all conceivable variations and combinations of the herein described embodiments are intended to be accommodated within the scope of the claims.

What is claimed is:

1. An absorbent, porous structure (4) comprising:
   a first absorbent region (19), primarily consisting of a first material, which stands in direct connection with a second absorbent region (20), primarily consisting of a second material that is hydrophilic,
   wherein the first material is hydrophilic and exhibits a receding wetting angle $\theta_r$ which is essentially as large as, or smaller than the receding wetting angle $\theta_r$ of the second material in an un-treated condition,
   wherein the first material comprises an agent that raises the receding wetting angle $\theta_r$ of the first material above the value for the receding wetting angle $\theta_r$ of the second material, the combination of the agent and the first material still being hydrophilic, whereby the receding wetting angle $\theta_r$ is larger for the first material than for the second material, and whereby liquid transport between the two regions (19, 20) takes place in a direction from the first region (19) to the second region (20) at least when the porous structure (4) is wet.

2. An absorbent structure (4) according to claim 1, characterized in that also the advancing wetting angle $\theta_a$ is larger for the first material than for the second material, whereby liquid transport between the two regions (19, 20) takes place in a direction from the first region (19) to the second region (20) irrespectively of whether the structure (4) is dry or wet.

3. An absorbent structure (4) according to claim 1, characterized in that the average pore size in the absorbent structure (4) is larger within the first region (19) than within the second region (20).

4. An absorbent structure (4) according to claim 1, characterized in that the first region is constituted of a first layer (19) in the absorbent structure (4), and that the second region is constituted of a second layer (20) in the absorbent structure (4), and wherein the two layers (19, 20) stand in direct connection with each other via surfaces of the layers bearing against each other.

5. An absorbent structure according to claim 1, characterized in that the two regions (49, 50; 49', 50') are constituted of parts of one and the same material layer (34).

6. An absorbent structure according to claim 5, characterized in that the first region (49') and the second region (50') are arranged alongside each other in the plane of the material layer (34).

7. An absorbent structure according to claim 5, characterized in that the two regions (49, 50) are arranged alongside each other in the thickness direction of the material layer (34).

8. An absorbent structure according to claim 1, characterized in that it exhibits additional regions with absorbent material, wherein the materials in the different regions comprised in the absorbent structure exhibit different receding wetting angles $\theta_r$ between themselves.

9. An absorbent structure according to claim 8, characterized in that the fibre structure is substantially planar with a first surface and a second surface parallel to the plane of the structure and with a thickness direction perpendicular to the plane, wherein the different regions are mutually arranged so that the structure exhibits a wetting angle gradient in the thickness direction and/or the plane of the structure.

10. An absorbent structure according to claim 1, characterized in that the first region (19; 49) primarily consists of cellulose fluff pulp manufactured in a chemi-thermomechanical way (CTMP), and that the second region (20; 50) consists of cellulose fluff pulp manufactured in a chemical way (CP).

11. An absorbent structure according to claim 10, characterized in that the agent for raising the receding wetting angle $\theta_r$ is poly-n-isopropylacryloamide (PNIPAM).

12. An absorbent structure according to claim 1, characterized in that the agent for raising the receding wetting angle $_r$ is applied in the structure by means of spraying.

13. An absorbent structure according to claim 1, characterized in that the agent for raising the receding wetting angle $\theta_r$ is applied in the fibre structure by means of coating the material with a liquid containing the agent.

14. The structure of claim 1, wherein the receding wetting angle of the untreated first material is about 0°–20° and the receding wetting angle of the combination of the first material and the agent is about 40° higher than the untreated receding wetting angle.

15. An absorbent, porous structure (4) comprising:
    a first absorbent region (19), primarily consisting of a first material, which stands in direct connection with a second absorbent region (20), primarily consisting of a second material that is hydrophilic,
    wherein the first material is hydrophilic and exhibits a receding wetting angle $\theta_r$ which is essentially as large as, or smaller than the receding wetting angle $\theta_r$ of the second material in an un-treated condition,
    wherein the first material comprises an agent that raises the receding wetting angle $\theta_r$ of the first material above the value for the receding wetting angle $\theta_r$ of the second material, the combination of the agent and the first material still being hydrophilic, whereby the receding wetting angle $\theta_r$ is larger for the first material than for the second material, and whereby liquid transport between the two regions (19, 20) takes place in a direction from the first region (19) to the second region (20) at least when the porous structure (4) is wet,
    wherein the agent for raising the receding wetting angle $\theta_r$ is ethylhydroxy-ethylcellulose (EHEC).

16. An absorbent article comprising:
    a liquid-pervious cover layer (2; 32), a liquid-impervious cover layer (3; 33) and an absorbent body (4; 34) enclosed between the two cover layers (2, 3; 32, 33);
    the absorbent body (4; 34) including a first absorbent region (19; 49), primarily consisting of a first material, which stands in direct connection with a second absorbent region (20; 50), primarily consisting of a second material that is hydrophilic,
    wherein the first material is hydrophilic and exhibits a receding wetting angle $\theta_r$ which is essentially as large as, or smaller than the receding wetting angle $\theta_r$ of the second material in an un-treated condition, wherein the first material comprises an agent that raises the receding wetting angle $\theta_r$ of the first material above the value for the receding wetting angle $\theta_r$ of the second material, the combination of the agent and the first material still being hydrophilic, whereby the receding wetting angle $\theta_r$ is larger for the first material than for the second material, and whereby liquid transport takes place between the two regions (19, 20; 49, 50) in a direction from the first region (19; 49) to the second region (20; 50) at least when the absorbent body (4; 34) is wet.

17. An absorbent article according to claim 16, characterized in that the first region (19) is constituted of a first layer (19) in the absorbent body (4), the second region (20) is constituted of a second layer (20) in the absorbent body (4), wherein the two layers (19, 20) stand in direct connection with each other via surfaces on the layers (19, 20) bearing on each other, and wherein the first layer (19) faces towards the liquid-pervious cover layer (2) and the second layer (20) faces towards the liquid-impervious cover layer (3).

18. An absorbent article according to claim 16, characterized in that the two regions (49, 50; 49', 50') are constituted of parts of one and the same material layer in the absorbent body (34).

19. An absorbent article according to claim 18, characterized in that the first region and the second region (49', 50') are arranged alongside each other in the plane of the material layer.

20. An absorbent article according to claim 18, characterized in that the two regions (49, 50) are arranged alongside each other in the thickness direction of the material layer.

21. An absorbent article according to claim 16, and further exhibiting two end portions (6, 7; 37, 38) and a crotch portion (8; 39), arranged between the end portions (8; 39), intended to be arranged in the crotch of a user during use and thereby to serve as a reception region for the body fluid which is emitted to the article, characterized in that the first region (19; 49), exhibiting the first material, primarily is located in the crotch portion (8; 39) of the article.

22. An absorbent article according to claim 16, characterized in that the advancing wetting angle $\theta_a$ is larger for the first material than for the second material, whereby liquid transport takes place between the two regions (19, 20; 49, 50) in a direction from the first region (19; 49) to the second region (20; 50) irrespectively of whether the absorbent body (4; 34) is dry or wet.

23. An absorbent structure according to claim 16, wherein the agent for raising the receding wetting angle $\theta_r$ is ethylhydroxy-ethylcellulose (EHEC).

24. The article of claim 16, wherein the receding wetting angle of the untreated first material is about 0°–20° and the receding wetting angle of the combination of the first material and the agent is about 40° higher than the untreated receding wetting angle.

* * * * *